United States Patent [19]

Goddard

[11] 4,164,513

[45] Aug. 14, 1979

[54] AMINO-SUBSTITUTED GUANIDINE SALTS OF DECAHYDRODECABORIC ACID

[75] Inventor: Terrence P. Goddard, Aptos, Calif.

[73] Assignee: Teledyne McCormick Selph, an operating div. of Teledyne Ind., Inc., Hollister, Calif.

[21] Appl. No.: 853,918

[22] Filed: Nov. 22, 1977

[51] Int. Cl.$^2$ .......................................... C07C 123/00
[52] U.S. Cl. .................................. 260/564 D; 149/22
[58] Field of Search ................ 260/564 D; 149/109.4, 149/22

[56] References Cited

U.S. PATENT DOCUMENTS

| 4,002,681 | 1/1977 | Goddard ........................... 149/22 X |
| 4,094,712 | 6/1978 | Goddard et al. .................. 149/22 X |

*Primary Examiner*—Stephen J. Lechert, Jr.
*Attorney, Agent, or Firm*—David H. Semmes; Warren E. Olsen

[57] ABSTRACT

This invention relates to amino-substituted guanidine decahydrodecaborates, which are shown to be novel boron-containing salts that have particular utility as high energy monopropellants. The invention includes the diamino-guanidinium and monoaminoguanidinium salts of decahydrodecaboric acid, and as preferred products of processes for preparing same.

4 Claims, No Drawings

AMINO-SUBSTITUTED GUANIDINE SALTS OF DECAHYDRODECABORIC ACID

CROSS-REFERENCE TO RELATED APPLICATIONS

This is a related application to my copending application of common assignment entitled BIS-TRIAMINOGUANIDINE DECAHYDRODECABORATE AND A PROCESS FOR ITS PREPARATION, filed Jan. 24, 1977 and assigned Ser. No. 762,229.

BACKGROUND AND BRIEF DESCRIPTION OF THE INVENTION

Boron hydride salts, in particular the non-metal salts of decahydrodecaboric acid, had been discovered to have particular utility in the field of high energy fuels. They may be used as constituents of pyrotechnic compositions and in propellants. For example, non-metallic salts of the decahydrodecaborate ion, and exemplary uses, are disclosed in the copending applications of common assignment entitled IGNITION AND PYROTECHNIC COMPOSITIONS, Ser. No. 694,625, filed June 10, 1976, and COPRECIPITATED PYROTECHNIC COMPOSITION PROCESSES AND RESULTANT PRODUCTS, Ser. No. 694,626, filed June 10, 1976.

The present invention teaches new non-metal salts of decahydrodecaboric acid, which exhibits stable physical properties, and are themselves high energy monopropellants. The compounds are very unusual in that they contain only boron, nitrogen, carbon and hyrogen, but no oxygen.

A particular objective in preparing compounds suitable for certain types of pyrotechnic usage is to achieve a high gas output and low molecular weight combustion products, when the compound is burned. Combustion products such as hydrogen ($H_2$) and nitrogen ($N_2$) gas fulfill this requirement. In preparing salts useful as pyrotechnic fuels from an anion such as decahydrodecaborate ($-2$) ($B_{10}H_{10}^{-2}$), it has been found advantageous to use a cation containing a high weight fraction of atomic nitrogen and hydrogen. Cations of the general formula $C(NHR)_3$ where R may be hydrogen (H) or an amino radical ($-NH_2$) are found to be such cations. In addition, the corresponding Bronsted bases of the free ions are strong bases, thus imparting to the cations and therefore the salts a high degree of chemical stability.

Other decahydrodecaborate ($-2$) salts employing guanidine chemistry have been previously investigated by the present inventor. The simple guanidine salt is disclosed in my earlier application BIS-GUANIDINIUM DECAHYDRODECABORATE AND A PROCESS OF ITS PREPARATION, Ser. No. 694,627, filed June 10, 1976, which is now U.S. Pat. No. 4,002,681. This simple salt was found to be useful as a high energy pyrotechnic fuel, and was by itself thermochemically stable; i.e., it has a substantial negative heat of formation as commonly defined by those practiced in the art. The fully amino-substituted compound is disclosed in my copending application of common assignment entitled BIS-TRIAMINOGUANIDINIUM DECAHYDRODECABORATE AND A PROCESS FOR ITS PREPARATION, Ser. No. 762,229, filed Jan. 24, 1977. In contast to the simple guanidine salt, the triaminoguanidine salt is a powerful monopropellant; i.e., combusts by itself releasing internal energy, without need of additional oxidizer materials.

The subject of the present invention is the mono- and diamino substituted guanidine salts, which like the triaminoguanidine salts, have been discovered to be monopropellants. As a result, the compounds taught herein are useful as monopropellants in their own right, or alternatively, can be used with additional oxidizer to modify combustion properties. Specifically, such inorganic oxidizing agents as potassium nitrate, guanidine nitrate, triaminoguanidine nitrate and ammonium perchlorate may advantageously be employed, in concentrations from 0–90%, by weight.

DETAILED DESCRIPTION OF THE INVENTION

The aminoguanidine$^{(A)}$ and diaminoguanidine$^{(B)}$ salts of the decahydrodecaborate ($-2$) ion are represented by the chemical formulae $(CNHNH_2(NH_2)_2)_2B_{10}H_{10}$ and $(C(NHNH_2)_2NH_2)_2B_{10}H_{10}$ respectively, or more accurately by the structural formulae:

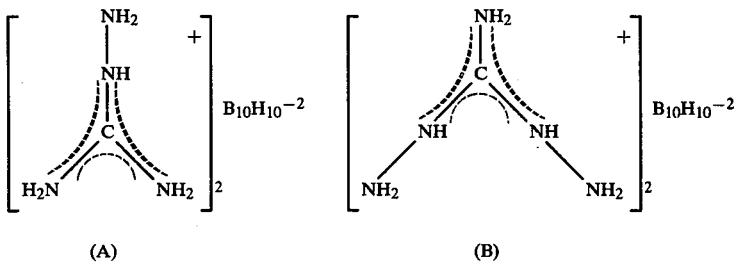

(A)  (B)

which illustrate the resonance stabilization achieved by protonating the free bases to form the unipositive ions.

Both of the salts may be conveniently prepared by neutralizing one mole of aqueous decahydrodecaboric acid $H_2B_{10}H_{10}$, with two moles of the free base corresponding to the desired cation, or with a salt, such as a carbonate, of the cation, which is degraded during the neutralization.

The aqueous decahydrodecaboric acid used as a starting material for the process of this invention is conveniently prepared by passing an amine or metal salt of decahydrodecaborate ($-2$) ion through a column containing a strongly acidic ion exchange resin of the sulfonic acid type, such as a DUOLITE type C-20, manufactured by the Diamond Shamrock Corporation. Preferred starting salts are bis (triethylammonium) decahydrodecaborate ($-2$) and disodium decahydrodecaborate ($-2$). The preparation and properties of the aqueous acid itself are known, and reference may be made to Knoth, U.S. Pat. No. 3,148,939, for further detail.

The free base of the desired cation may be prepared by passing a chloride, nitrate, or other water soluble salt of the cation through a column containing a strongly basic ion exchange resin of the polystyrene type, such as DOWEX ® 2-X8.

The neutralization reaction yields the constituent ions in aqueous solution. The salt may be recovered by a variety of standard methods, for example by evaporating the solution to near saturation and chilling, or by precipitating the salt from solution with a nonsolvent.

The subjects of this invention are useful as high energy monopropellants in such devices as electric initiators or squibs, or as ingredients to enhance burning rates. The compounds may be mixed with additional materials with oxidative power to modify the combustion properties, for use in such devices as pyrotechnic deflagrating cords.

Specific reference should be had to the above-noted copending application entitled IGNITION AND PYROTECHNIC COMPOSITIONS, Ser. No. 694,625, incorporated herein by reference, for examples of suitable and preferred species of oxidizing agents which are useful for creating a pyrotechnic mixture with the particular boron-containing salt taught herein. While the $B_{10}H_{10}^{-2}$ anion, a bicapped square antiprism polyhedral ion, has unusual stability, it is significant that the present compounds achieve a resonance stabilization by protonating a free substituted guanidine base to form the unipositive ion comprising the cation. Of greater, and perhaps related, significance is the unexpected result that the simple salt bis-guanidinium decahydrodecaborate, had a substantial negative heat of formation, making the simple salt useful as a high energy pyrotechnic fuel, while the present invention exhibits compounds having substantial internal energy. Hence, the compounds taught herein are useful alone, as monopropellants, or optionally are capable of use as components in a pyrotechnic material, through mixture with an oxidizing agent, to take further advantage of the unique decomposition properties of the decahydrodecaborate (−2) anion.

The unique products of this invention, mono and di-amino substituted guanidinium decahydrodecaborates, are further illustrated by reference to the following examples:

EXAMPLE I

Bis-Aminoguanidinium Decahydrodecaborate (−2)

Preparation

One hundred fifty (150) milliliters of aqueous decahydrodecaboric acid, approximately 0.25 M, is neutralized directly to pH 7 with solid aminoguanidine bicarbonate. Vigorous evolution of carbon dioxide is apparent. The resulting solution is slowly poured into 8 parts-by-volume isopropanol, with vigorous stirring. A white, fluffy solid precipitates immediately. The precipitate is filtered and washed with butyl acetate. The salt is oven dried at 60° C., at the end of which it is a pink color. Overall yield of the reaction is 90%.

Analysis

The $B_{10}H_{10}^{-2}$ in a small sample of the compound is oxidized at 80° C. with platinum black in aqueous solution to boric acid. The boric acid content of the degraded product is determined by titration against sodium hydroxide in mannitol solution. Boron content found: 38.9%. Theoretical content: 40.3%.

The infrared spectrum is obtained in a KBr pellet incorporating the compound. The spectrum between 4000 and 800 cm$^{-1}$ is compared with spectra of aminoguanidinium nitrate dihydrate and metallic salts of decahydrodecaboric acid. The characteristic peaks from the aminoguanidinium ion are found at 3400, 1700, 1200 and 900 cm$^{-1}$; the characteristic decahydrodecaborate (−2) ion peaks are found at 2470, 1080 and 1030 cm$^{-1}$.

An analysis of solution conductivity vs. solution concentration gives a conductivity of 262 ohm$^{-1}$ cm$^2$ mole$^{-1}$ at infinite dilution, which is characteristic of a compound containing three ions, one species being an organic cation. The above analyses demonstrate that the recovered product is the desired subject of the invention.

EXAMPLE II

Bis N,N'Diaminoguanidinium Decahydrodecaborate (−2)

Preparation

One hundred forty (140) milliliters of aqueous decahydrodecaboric acid, approximately 0.25 M, is neutralized directly to pH 7 with N,N'diaminoguanidine free base. The aqueous free base is obtained by passing a 0.8 M solution of N,N'diaminoguanidine hydrochloride through a column containing DOWEX ® 2-X8 strongly basic ion exchange resin. The resulting solution is slowly poured into 8 parts-by-volume isopropanol, with vigorous stirring. A white precipitate forms immediately. The precipitate is filtered and washed with butyl acetate, and oven dried at 60° C. A white, fluffy powder is recovered, yield approximately 80%.

Analysis

The $B_{10}H_{10}^{-2}$ in a small sample of the compound is oxidized at 80° C. with platinum black in aqueous solution to boric acid. The boric acid content of the degraded product is determined by titration against sodium hydroxide in mannitol solution. Boron content found: 36.2%. Theoretical content: 35.9%.

The infrared spectrum is obtained in a KBr pellet incorporating the compound. The spectrum between 4000 and 800 cm$^{-1}$ is virtually a superposition of spectra of N,N'diaminoguanidine hydrochloride and metallic salts of decahydrodecaboric acid with some minor shifting due to lattice efforts. The characteristic peaks from the triaminoguanidinium ion are found at 3300, 1700, 1390, 1200, 1000, and 960 cm$^{-1}$; the characteristic decahydrodecaborate (−2) ion peaks are found at 2470, 1080 and 1030 cm$^{-1}$.

An analysis of solution conductivity vs. solution concentration gives a conductivity of 280 ohm$^{-1}$ cm$^2$ mole$^{-1}$ at infinite dilution, which is characteristic of a compound containing three ions, one species being an organic cation. The above analyses demonstrate that the recovered product is the desired subject of the invention.

EXAMPLE III

Pyrotechnic Characteristics

The pyrotechnic utility of the subject compositions is demonstrated by subjecting the materials to several standard tests used to characterize explosives and pyrotechnics. Results are summarized in Table I.

| MATERIAL | "NO FIRE" IMPACT (cm) | HEAT OF EXPLOSION (cal/g) | AUTOIGNITION (°C.) |
|---|---|---|---|
| bis-aminoguanidinium decahydrodecaborate | 16 | 1228 | 292 |
| bis N,N'diaminoguanidinium decahydrodecaborate | 1 | 1556 | 273 |

TABLE I
PYROTECHNIC CHARACTERISTICS

A sample of the compound, is subjected to an impact drop test, consisting of placing a 5 milligram sample of the powder on a 400 grit paper disc, and releasing a 2 kilogram weight from a calibrated height. An anvil on the weight strikes the powder sample. The release height at which the sample fails to ignite 10 times in succession is recorded as the impact sensitivity "no fire."

The heat of explosion of the compound is measured by igniting a sample of the compound in a closed calorimeter bomb under argon, and measuring the temperature rise in a water bath surrounding the bomb. The results are customarily reported in calories of heat liberated per gram of explosive.

The autoignition temperature of the compound is measured by recording the temperature at which the compound will not spontaneously ignite within 5 seconds when placed in contact with a hot reservoir.

The data in Table I show that the aminoguanidine decahydrodecaborate salt is a relatively sensitive pyrotechnic composition with good heat output; it is useful as a transfer material in pyrotechnic trains or as a burning rate modified in propellants. The N,N'diaminoguanidinium decahydrodecaborate salt is very sensitive, with caloric output over four times that of a conventional initiating explosive such as lead azide. It is useful as a new type of initiating (priming) explosive, and as well, could be used as a propellant burning rate modifier when suitably combined with oxidizer. Both compounds are stable in excess of 200° C. as evidenced by differential scanning calorimeter studies, which is of substantial benefit to high temperature explosive applications.

Obvious modifications and equivalents within the present invention will appear to those of ordinary skill in the art, and the present invention is to be defined solely by the scope of the appended claims.

I claim:
1. The monoaminoguanidinium salt of decahydrodecaboric acid, having the formula $(CNHNH_2(NH_2)_2)_2B_{10}H_{10}$.
2. The monoaminoguanidine salt of the decahydrodecaborate (−2) ion as represented by the structural formula:

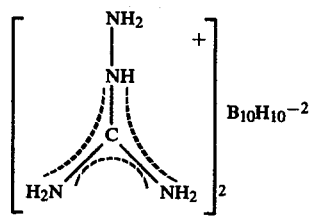

wherein resonance stabilization is achieved by protonating a free guanidine base to form the unipositive ion.

3. The diaminoguanidine salt of decahydrodecaboric acid, having the formula $(C(NHNH_2)_2NH_2)_2B_{10}H_{10}$.
4. The diaminoguanidine salt of the decahydrodecaborate (−2) ion as represented by the structural formula:

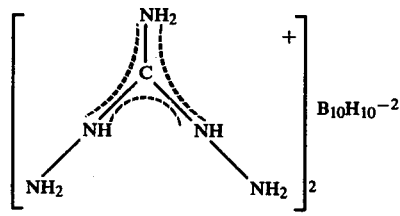

wherein resonance stabilization is achieved by protonating a free substituted guanidine base to form the unipositive ion.

* * * * *